United States Patent
Elia et al.

(10) Patent No.: US 10,588,493 B2
(45) Date of Patent: Mar. 17, 2020

(54) SHEATH AND HUB FOR IMAGING ENDOSCOPE

(71) Applicant: ART Healthcare Ltd., Natania (IL)

(72) Inventors: Liron Elia, Kiryat-Ata (IL); Gavriel J. Iddan, Haifa (IL)

(73) Assignee: ART Healthcare Ltd., Natania (IL)

( * ) Notice: Subject to any disclaimer, the term of this patent is extended or adjusted under 35 U.S.C. 154(b) by 0 days.

(21) Appl. No.: 16/159,796

(22) Filed: Oct. 15, 2018

(65) Prior Publication Data

US 2019/0046017 A1     Feb. 14, 2019

Related U.S. Application Data

(63) Continuation of application No. 15/353,865, filed on Nov. 17, 2016, now Pat. No. 10,098,523.
(Continued)

(51) Int. Cl.
*A61B 1/00*     (2006.01)
*A61B 1/015*     (2006.01)
(Continued)

(52) U.S. Cl.
CPC ...... *A61B 1/00142* (2013.01); *A61B 1/00068* (2013.01); *A61B 1/00119* (2013.01);
(Continued)

(58) Field of Classification Search
CPC ... A61B 1/00142; A61B 1/01; A61B 1/00068; A61B 1/00119; A61B 1/12; A61B 1/015;
(Continued)

(56) References Cited

U.S. PATENT DOCUMENTS

| | | |
|---|---|---|
| 4,769,014 A | 9/1988 | Russo |
| 4,801,297 A | 1/1989 | Mueller |
| | (Continued) | |

FOREIGN PATENT DOCUMENTS

| | | |
|---|---|---|
| EP | 1557192 | 7/2005 |
| WO | WO 2009/006335 | 1/2009 |
| | (Continued) | |

OTHER PUBLICATIONS

Advisory Action Before the Filing of an Appeal Brief dated Feb. 2, 2017 From the US Patent and Trademark Office Re. U.S. Appl. No. 14/342,382. (4 pages).
(Continued)

*Primary Examiner* — Timothy J Neal

(57) ABSTRACT

A compound sheath comprising: an endoscopic channel arranged for accepting an elongated endoscopic imaging device; a parallel use channel arranged for accepting a catheter-based tool, and a multi-channel hub that couples to the proximal end of the parallel use channel comprising: a rinse port that couples to a fluid reservoir device that injects fluid; a withdrawal port that couples to a vacuum forming device that removes fluid; a tool port for passing a catheter-based tool; wherein the multi-channel hub establishes a fluid channel for fluid communication between the parallel use channel and the rinse port or the withdrawal port, and a mechanical channel for passing therethrough a catheter-based tool between the parallel use channel and the tool port such that fluid from the rinse port or the withdrawal port and the catheter-based tool of the tool port are simultaneously passing all along the parallel use channel.

10 Claims, 13 Drawing Sheets

Related U.S. Application Data

(60) Provisional application No. 62/256,721, filed on Nov. 18, 2015.

(51) Int. Cl.
  A61B 1/018 (2006.01)
  A61B 1/01 (2006.01)
  A61B 1/12 (2006.01)

(52) U.S. Cl.
  CPC ............ A61B 1/00135 (2013.01); A61B 1/01 (2013.01); A61B 1/015 (2013.01); A61B 1/018 (2013.01); A61B 1/12 (2013.01); *A61B 1/00066* (2013.01); *A61B 1/00103* (2013.01); *A61B 2560/04* (2013.01)

(58) Field of Classification Search
  CPC . A61B 1/00135; A61B 1/018; A61B 1/00066; A61B 1/00103; A61B 2560/04
  See application file for complete search history.

(56) References Cited

U.S. PATENT DOCUMENTS

| | | | |
|---|---|---|---|
| 4,911,148 A | 3/1990 | Sosnowski et al. | |
| 5,179,934 A | 1/1993 | Nagayoshi et al. | |
| 5,665,064 A | 9/1997 | Bodicky et al. | |
| 5,860,953 A | 1/1999 | Snoke et al. | |
| 6,254,061 B1 | 7/2001 | Levine et al. | |
| 6,322,495 B1 | 11/2001 | Snow et al. | |
| 6,425,535 B1* | 7/2002 | Akiba | A61B 1/00068 134/21 |
| 7,344,494 B2 | 3/2008 | Hoeg et al. | |
| 8,361,041 B2 | 1/2013 | Fang et al. | |
| 8,678,999 B2 | 3/2014 | Isaacson | |
| 9,060,922 B2 | 6/2015 | Nieman et al. | |
| 9,526,674 B2 | 12/2016 | Heyns et al. | |
| 2002/0077593 A1 | 6/2002 | Perkins et al. | |
| 2002/0138126 A1* | 9/2002 | Camrud | A61F 2/95 623/1.11 |
| 2005/0020974 A1 | 1/2005 | Noriega et al. | |
| 2005/0197534 A1 | 9/2005 | Barbato et al. | |
| 2006/0116552 A1 | 6/2006 | Noguchi et al. | |
| 2007/0015968 A1 | 1/2007 | Shelnutt | |
| 2007/0203393 A1 | 8/2007 | Stefanchik | |
| 2008/0228066 A1 | 9/2008 | Waitzman | |
| 2009/0275825 A1 | 11/2009 | Thomas | |
| 2009/0318798 A1 | 12/2009 | Singh et al. | |
| 2010/0280316 A1 | 11/2010 | Dietz et al. | |
| 2011/0015487 A1 | 1/2011 | Matasov | |
| 2012/0116160 A1 | 5/2012 | Nieman et al. | |
| 2014/0330076 A1 | 11/2014 | Elia et al. | |
| 2015/0025311 A1* | 1/2015 | Kadan | A61B 17/3474 600/104 |
| 2015/0196193 A1* | 7/2015 | Kienzle | A61B 1/00066 600/109 |
| 2017/0135560 A1 | 5/2017 | Elia et al. | |
| 2017/0143446 A1* | 5/2017 | Kolbel | A61F 2/95 |

FOREIGN PATENT DOCUMENTS

| | | |
|---|---|---|
| WO | WO 2009/115914 | 9/2009 |
| WO | WO 2010/118256 | 10/2010 |
| WO | WO 2013/030775 | 3/2013 |
| WO | WO 2017/085724 | 5/2017 |

OTHER PUBLICATIONS

Applicant-Initiated Interview Summary dated Jul. 21, 2017 From the US Patent and Trademark Office Re. U.S. Appl. No. 14/343,382. (3 pages).
Communication Pursuant to Rule 164(1) EPC and the Supplementary Partial European Search Report dated Mar. 10, 2015 From the European Patent Office Re. Application No. 12827550.0.
European Search Report and the European Search Opinion dated Nov. 8, 2016 From the European Patent Office Re. Application No. 16182381.0. (7 Pages).
International Preliminary Report on Patentability dated Mar. 13, 2014 From the International Bureau of WIPO Re. Application No. PCT/IB2012/054442.
International Preliminary Report on Patentability dated May 31, 2018 From the International Bureau of WIPO Re. Application No. PCT/IL2016/051240. (12 Pages).
International Search Report and the Written Opinion dated Feb. 3, 2017 From the International Searching Authority Re. Application No. PCT/IL2016/051240. (17 Pages).
International Search Report and the Written Opinion dated Jan. 14, 2013 From the International Searching Authority Re. Application No. PCT/IB2012/054442.
Official Action dated Mar. 7, 2017 From the US Patent and Trademark Office Re. U.S. Appl. No. 14/342,382. (11 pages).
Official Action dated Dec. 21, 2017 From the US Patent and Trademark Office Re. U.S. Appl. No. 15/353,865. (22 pages).
Official Action dated May 25, 2016 From the US Patent and Trademark Office Re. U.S. Appl. No. 14/342,382.
Official Action dated Oct. 31, 2016 From the US Patent and Trademark Office Re. U.S. Appl. No. 14/342,382.
Restriction Official Action dated Mar. 15, 2016 From the US Patent and Trademark Office Re. U.S. Appl. No. 14/342,382.
Restriction Official Action dated Sep. 25, 2017 From the US Patent and Trademark Office Re. U.S. Appl. No. 15/353,865. (7 pages).
Supplementary European Search Report and the European Search Opinion dated Jun. 29, 2015 From the European Patent Office Re. Application No. 12827550.0.

\* cited by examiner

SHEATH AND HUB FOR IMAGING ENDOSCOPE

RELATED APPLICATION

This application is a continuation of U.S. patent application Ser. No. 15/353,865 filed on Nov. 17, 2016 which claims the benefit of priority under 35 USC § 119(e) of U.S. Provisional Patent Application No. 62/256,721 filed Nov. 18, 2015.

The contents of the above applications are all incorporated by reference as if fully set forth herein in their entirety.

FIELD AND BACKGROUND OF THE INVENTION

The present invention, in some embodiments thereof, relates to endoscopic equipment and, more particularly, but not exclusively, to a compound sheath for an endoscope.

Endoscopes are used in minimally invasive medical procedures to provide the physician with a view inside lumens of the body. Endoscopes include working channels through which instruments may be introduced into the lumen to perform procedures.

A common problem of such endoscopes is the cleaning and sterilization between patients. The cleaning and sterilization is a tedious task that takes a relatively long period of time, providing increased costs and a slow turnaround for repeated use of the endoscope. Moreover, the cleaning procedure is sometimes performed improperly, placing the patient at risk of infection and complication.

One solution is a single use sheath that covers the endoscope, protecting the patient from contamination, with no need for the tedious cleaning procedure.

SUMMARY OF THE INVENTION

It is an object of the present invention to provide an apparatus, a system, and a method, for encasing an endoscope during an endoscopic procedure.

The foregoing and other objects are achieved by the features of the independent claims. Further implementation forms are apparent from the dependent claims, the description and the figures.

According to a first aspect, a compound sheath for encasing an endoscope during an endoscopic procedure, comprises: an endoscopic channel arranged as a first elongated lumen sized for accepting an elongated endoscopic imaging device; a parallel use channel arranged as a second elongated lumen sized for accepting a catheter-based tool, the walls of the parallel use channel arranged for flow of fluid through the parallel use channel; wherein the endoscopic channel and the parallel use channel are arranged parallel to each other along a longitudinal axis of the compound sheath; and a multi-channel hub including: a connection port that couples to the proximal end of the parallel use channel; a rinse port that couples to a fluid reservoir device that injects fluid; a withdrawal port that couples to a vacuum forming device that removes fluid; a tool port for passing a catheter-based tool; wherein the multi-channel hub establishes a fluid channel for fluid communication between the parallel use channel and the rinse port or the withdrawal port, and a mechanical channel for passing therethrough a catheter-based tool between the parallel use channel and the tool port such that fluid from the rinse port or the withdrawal port and the catheter-based tool of the tool port are simultaneously passing all along the parallel use channel.

The parallel use channel allows simultaneously performing multiple procedural acts, including introduction of catheter-based tools (e.g., wire-based) and injection of fluid (e.g., liquid) or removal of fluid (e.g., liquid).

In a first possible implementation of the sheath according to the first aspect, the parallel use channel is a single parallel use channel, and the connection port is a single connection port coupled to the single parallel use channel.

The multi-channel hub enables the single parallel use channel for simultaneous use by different connected devices to perform different procedural acts. The single channel design is compact, allowing introduction into narrow lumens.

In a second possible implementation form of the sheath according to the first aspect as such or according to any of the preceding implementation forms of the first aspect, the multi-channel hub includes a septum disposed at the tool port designed to prevent leaks of fluid out of the tool port when the catheter-based tool is inserted into the parallel use channel and fluid is flowing in the parallel use channel from the rinse port or to the withdrawal port.

In a third possible implementation form of the sheath according to the first aspect as such or according to any of the preceding implementation forms of the first aspect, the multi-channel hub includes a switch for selecting which of the rinse port, withdrawal port, and tool port is in communication with the parallel use channel using the connection port.

In a fourth possible implementation form of the sheath according to the third implementation form of the first aspect, the switch of the multi-channel hub is operated by rotation of a linking channel between the rinse port, withdrawal port, and tool port and the connection port.

In a fifth possible implementation form of the sheath according to the first aspect as such or according to any of the preceding implementation forms of the first aspect, the multi-channel hub is arranged as an H, wherein each of the four arms of the H includes one of: the connection port, the rinse port, the withdrawal port, and the tool port.

In a sixth possible implementation form of the sheath according to the fifth implementation form of the first aspect, a first arm of the H includes the connection port, an opposite arm of the H located along the longitudinal axis of the first arm includes the tool port arranged for introduction of the catheter-based tool into the parallel use channel using the connection port, and the two other arms of the H include the rinse port and the withdrawal port.

The tool is inserted in a straight direction through the opposite arms of the H.

In a seventh possible implementation form of the sheath according to the sixth implementation form of the first aspect, wherein the opposite arm including the tool port includes a septum designed to prevent leaks of fluid out of the multi-channel hub, the rinse port includes a first check valve designed to allow flow of liquid into the multi-channel hub and prevent backflow of liquid out of the multi-channel hub, and the withdrawal port includes a second check value designed to allow flow out of liquid out of the multi-channel hub and prevent backflow of liquid into the multi-channel hub.

In an eighth possible implementation form of the sheath according to the first aspect as such or according to any of the preceding implementation forms of the first aspect, the endoscopic channel has a diameter small enough to accept the elongated endoscopic imaging device that does not include an integrated parallel use channel within the body of the elongated endoscopic imaging device.

In a ninth possible implementation form of the sheath according to the first aspect as such or according to any of the preceding implementation forms of the first aspect, the sheath further comprises at least one illumination element located on a distal end portion of the compound sheath, the at least one illumination element designed to illuminate distal to the compound sheath in place of illumination elements of the elongated endoscopic imaging device.

In a tenth possible implementation form of the sheath according to the ninth implementation form of the first aspect, the multi-channel hub includes a power supply socket that supplies electrical power to the at least one illumination element.

In an eleventh possible implementation form of the sheath according to the first aspect as such or according to any of the preceding implementation forms of the first aspect, the elongated endoscopic imaging device comprises an imaging sensor at a distal end portion thereof, and a handle at a proximal end portion thereof, the handle includes an electrical interface for communication with a display for presenting images captured by the imaging sensor, and the handle includes a controller for adjusting the viewing direction of the distal end portion.

In a twelfth possible implementation form of the sheath according to the eleventh implementation form of the first aspect, the imaging sensor includes a 4 k imaging sensor.

In a thirteenth possible implementation form of the sheath according to the first aspect as such or according to any of the preceding implementation forms of the first aspect, the sheath further comprises a transparent optical window disposed at the distal end portion of the endoscopic channel, the transparent optical window is designed to prevent or reduce stray light from entering an imaging sensor of the elongated endoscopic device located within the endoscopic channel.

In a fourteenth possible implementation form of the sheath according to the first aspect as such or according to any of the preceding implementation forms of the first aspect, at least one of the rinse port and the withdrawal port includes a valve that controls the fluid communication between the respective rinse port or withdrawal port and the connection port.

In a fifteenth possible implementation form of the sheath according to the first aspect as such or according to any of the preceding implementation forms of the first aspect, the parallel use channel is open at the distal end thereof to provide fluid and mechanical communication between the parallel use channel and the body of the patient external to the compound sheath, and the endoscopic channel is closed to prevent fluid communication between the endoscopic channel and the body of the patient external to the compound sheath.

According to a second aspect, a method for operating a compound sheath of an endoscope, comprises: inserting an elongated endoscopic imaging device into an endoscopic channel of the compound sheath having a parallel use channel; establishing fluid communication between the parallel use channel and at least one of: a rinse port, and a withdrawal port of a multi-channel hub of the compound sheath; performing a first procedural act using the established fluid communication between the parallel use channel and at least one of: rinse port and withdrawal port; establishing a mechanical channel for passing therethrough a catheter-based tool between the parallel use channel and a tool port of the multi-channel hub; and performing a second procedural act using the catheter-based tool passed along the established mechanical channel between the parallel use channel and the tool port; wherein the first procedural act and the second procedural act are performed simultaneously.

Unless otherwise defined, all technical and/or scientific terms used herein have the same meaning as commonly understood by one of ordinary skill in the art to which the present invention pertains. Although methods and materials similar or equivalent to those described herein can be used in the practice or testing of embodiments of the present invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the present invention can involve performing or completing selected tasks manually, automatically, or a combination thereof. Moreover, according to actual instrumentation and equipment of embodiments of the method and/or system of the present invention, several selected tasks could be implemented by hardware, by software or by firmware or by a combination thereof using an operating system.

For example, hardware for performing selected tasks according to embodiments of the present invention could be implemented as a chip or a circuit. As software, selected tasks according to embodiments of the present invention could be implemented as a plurality of software instructions being executed by a computer using any suitable operating system. In an exemplary embodiment of the present invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the present invention are herein described, by way of example only, with reference to the accompanying drawings. With specific reference now to the drawings in detail, it is stressed that the particulars shown are by way of example and for purposes of illustrative discussion of embodiments of the present invention. In this regard, the description taken with the drawings makes apparent to those skilled in the art how embodiments of the present invention may be practiced.

In the drawings.

DESCRIPTION OF SPECIFIC EMBODIMENTS OF THE INVENTION

Figure 1:
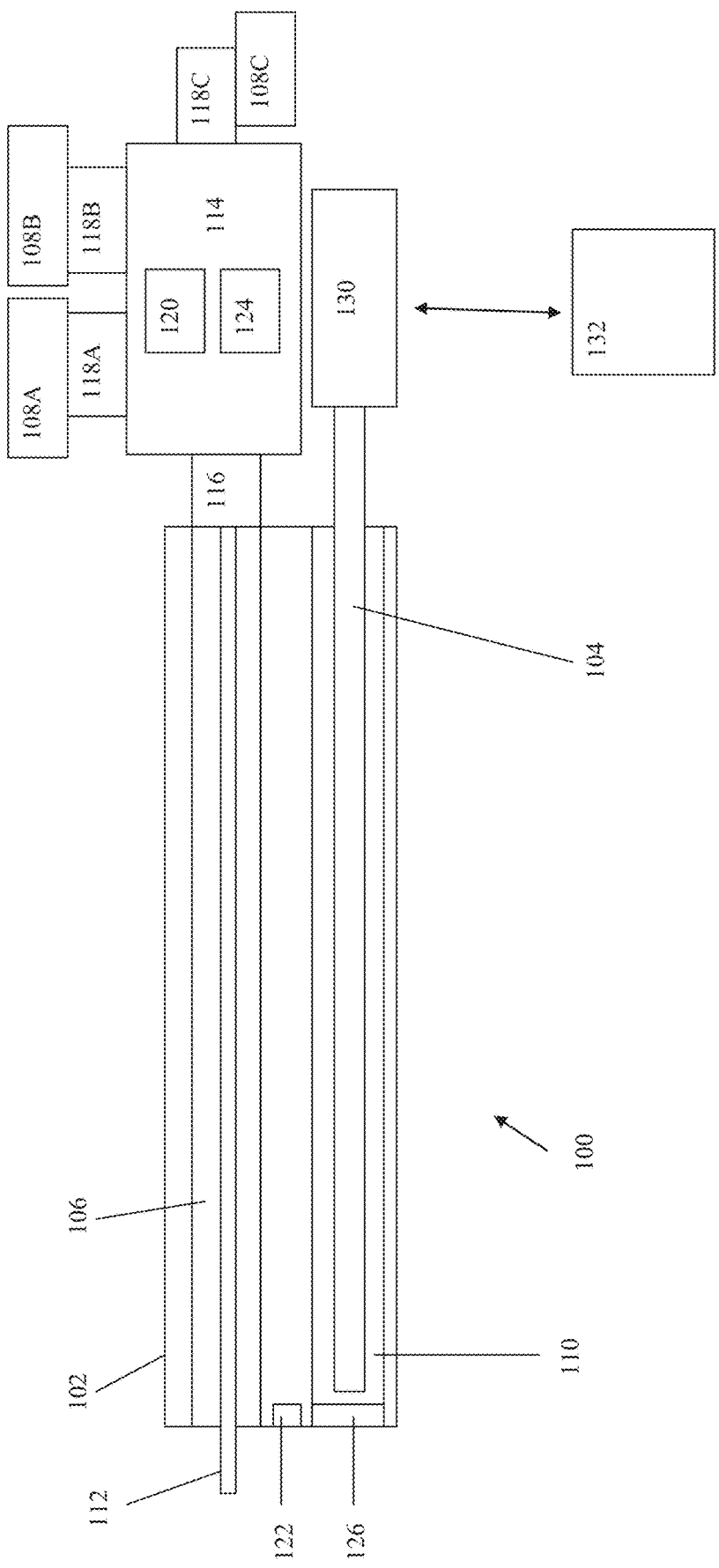
FIG. 1 is a is a block diagram of components of an endoscopic system that includes a compound sheath for encasing an endoscope during an endoscopic procedure, in accordance with some embodiments of the present invention.

The present invention, in some embodiments thereof, relates to endoscopic equipment and, more particularly, but not exclusively, to a compound sheath for an endoscope.

An aspect of some embodiments of the present invention relates to a compound sheath (e.g., single use, disposable) that includes an endoscopic channel for encasing an endoscope during an endoscopic procedure, and a parallel use channel for simultaneously performing multiple procedural acts, including introduction of catheter-based tools (e.g., wire-based) and injection of fluid (e.g., liquid) or removal of fluid (e.g., liquid). The compound sheath includes a multi-channel hub in communication with the parallel use channel. The multi-channel hub includes multiple working ports, each of which is used to access the common parallel use channel to perform a respective procedural act. The multi-channel hub enables the parallel use channel for simultaneous use by different connected devices to perform different procedural acts, for example, a needle is used to biopsy tissue, a water reservoir is used to inject water into the lumen of the patient in which the procedure is being performed, and a vacuum is used to remove excess water and other liquids from the lumen of the patient. The multi-channel hub establishes a fluid channel for fluid communication between the parallel use channel and a rinse port (that couples to a fluid reservoir device) or a withdrawal port (that couples to a vacuum forming device that removes fluid), and a mechanical channel for passing therethrough a catheter-based tool between the parallel use channel and a tool port such that fluid from the rinse port or the withdrawal port and the catheter-based tool of the tool port are simultaneously passing all along the parallel use channel.

Optionally, a switch (optionally implemented as a valve) connected to the multi-channel hub selects which of the working ports is currently the active working port that is in communication with the parallel use channel. The procedural act associated with the active working port may be performed using the parallel use channel. The switch activates a single working port at a time, preventing access to the parallel use channel from the other working ports. Port(s) may be equipped with plugs (e.g., septums) and/or valve(s) designed to prevent or reduce back flow of liquid (out of the parallel use channel) and/or mixing between port(s), optionally one way valves. Fluid port(s) and/or vacuum port(s) include valves (or other fluid sealing elements) designed to isolate the fluid and vacuum from other ports. The valve of the fluid port is designed to isolate the vacuum effect of the vacuum port from suctioning fluid from the fluid port. The value of the vacuum port is designed to isolate the device attached to the vacuum port from being injected with fluid when fluid is being inserted from the fluid port.

Alternatively, the multi-channel hub is operated without the switch, or includes a switch for each working port through which fluid is designated to flow in or out of the parallel use channel. The multi-channel hub with multiple switches may be set (or the switch-less multi-channel hub is designed to) provide simultaneous access to the common parallel use channel by multiple working ports. For example, an ablation catheter may be inserted through a first working port of the multi-channel hub to perform a tissue ablation procedure, while water is injected into the lumen that includes the tissue, or while liquid is removed from the lumen.

An aspect of some embodiments of the present invention relates to operating a sheath for encasing an endoscope. The endoscope is inserted into the endoscopic channel of the sheath. Multiple devices are connected to working ports of a multi-channel hub connected to a proximal end portion of a parallel use channel of the sheath, for example, a catheter-based tool for manipulating tissue, a liquid source for injection of liquid, and a suction device for removal of liquid. The sheath with encased endoscope is introduced into a lumen or cavity of the patient. A certain working port is selected using a switch, and/or the device connected to the certain working port is activated. Fluid communication is established between the parallel use channel and a rinse port or a withdrawal port of the multi-channel hub of the sheath.

A first procedural act is performed within the lumen or cavity using the parallel use channel of the sheath and the fluid communication channel, for example, injection of a rinsing saline solution. Another working port is selected using the switch, and/or another device connected to another working port is activated. A mechanical channel for passing therethrough a catheter-based tool between the parallel use channel and a tool port of the multi-channel hub is established. A second procedural act is performed within the lumen or cavity using the common parallel use channel of the sheath and the mechanical channel, for example, biopsy or ablation of tissue using the catheter-based tool. Optionally, the first and second procedural acts are performed simultaneously by access of the parallel use channel. Additional parallel use channels and/or devices may be activated and used in performing additional procedural acts within the lumen or cavity using the parallel use channel of the sheath.

Before explaining at least one embodiment of the present invention in detail, it is to be understood that the present invention is not necessarily limited in its application to the details of construction and the arrangement of the components and/or methods set forth in the following description and/or illustrated in the drawings and/or the Examples. The present invention is capable of other embodiments or of being practiced or carried out in various ways.

As used herein, the terms proximal and distal are used with reference to the operator of the endoscope located within the sheath. The term proximal means relatively closer to the operator of the endoscope located within the sheath. The term distal means relatively further away from the operator of the endoscope located within the sheath.

As used herein, the terms endoscope and elongated endoscopic imaging device may be interchanged.

As used herein, the terms compound sheath and sheath are interchangeable. As used herein, the term compound sheath means a sheath that includes the parallel use channel and the endoscopic channel.

Reference is now made to FIG. 1, which is a block diagram of components of an endoscopic system 100 that includes a sheath 102 for encasing an endoscope 104 during an endoscopic procedure, in accordance with some embodiments of the present invention. Sheath 102 includes a parallel use channel 106 that may be accessed simultaneously and/or sequentially using multiple devices 108A-C each designed for performing a respective procedural act. Optionally, parallel use channel 106 is a single channel.

Sheath 102 is designed to be disposable, for single use with a single patient. For example, sheath 102 is made from plastic. Sheath 102 prevents or reduces risk of cross-patient contamination from improper sterilization of endoscope 104, while providing improved ability to perform multiple procedural acts.

Sheath 102 includes an endoscopic channel 110 for accepting endoscope 104. Endoscopic channel 110 is designed as an elongated lumen, optionally a tube, having an internal dimension (e.g., diameter) that is larger than the external dimension (e.g., diameter) of endoscope 104. Endoscopic channel 110 has a diameter small enough to accept endoscope 104 that does not include an integrated parallel use channel within the body of endoscope 104.

Optionally, endoscope 104 does not include a working channel (in comparison to traditional endoscopes that have a working channel within the body of the endoscope). The working channel for use with endoscope 104 is provided by parallel use channel 106 of sheath 102.

Endoscope 104 includes a controller 130 to control the direction of the distal end portion of endoscope 104. Controller 130 may be positioned at the proximal end portion of endoscope 104 that remains outside of the body of the patient. Controller 130 may be implemented within a handle, for example, as a thumb wheel that is rotated.

Endoscope 104 is in electrical communication (e.g., using a wire(s) and/or wireless connection, located locally or remotely over a network) with one or more display devices 132 for presenting image(s) captured by the imaging sensor of endoscope 104. Communication may be provided using controller 130 and/or the proximally located handle, for example, using a USB port, and/an antenna (e.g., to establish a network connection, such as a short range network). Exemplary display devices 132 include a smartphone, a tablet computer, and a monitor hanging on a wall. Additional details of exemplary endoscopes 104 are described herein with reference to FIG. 3. One or more display devices 132 may be remotely located (communicated with over a network connection). The remotely located physicians may observe the remote procedure, for example, to provide real-time consultation to locations without in-house experts.

Sheath 102 includes parallel use channel 106. Parallel use channel 106 is designed as an elongated lumen, optionally a tube, arranged parallel to endoscopic channel 110 along the longitudinal axis of sheath 102. Parallel use channel 106 may be in fluid isolation from endoscopic channel 110, such that liquid within parallel use channel 106 does not enter endoscopic channel 110. Parallel use channel 106 may be open at its distal end, to allow catheter-based tools inserted within parallel use channel 106 to access tissues of the patient. The open end of parallel use channel 106 provides fluid and/or mechanical communication between the parallel use channel and the body of the patient external to the sheath. Endoscopic channel 110 is closed (e.g., hermetically sealed) at least at the portion of sheath 102 that enters the body of the patient, to prevent contamination of and/or by the patient. The closed endoscopic channel 110 prevents fluid communication between the endoscopic channel and the body of the patient external to the sheath The internal dimension (e.g., diameter) of parallel use channel 106 may be smaller, approximately equal to, or larger than the internal dimension (e.g., diameter) of endoscopic channel 110. The internal dimension of parallel use channel 106 is selected according to the external dimension (e.g., diameter) of a catheter-based tool 112 inserted using parallel use channel 106. The walls of parallel use channel 106 are designed or flow of liquid in and/or out of parallel use channel 106, for example, saline (which may be injected into the patient through parallel use channel 106), and/or blood (which may be extracted from the patient through parallel use channel 106).

Sheath 102 includes a multi-channel hub 114. Multi-channel hub 114 may be integrated within sheath 102, for example, created using an injection molding process that creates sheath 102 and multi-channel hub 114 as a single unit. Multi-channel hub 114 may be attachable to parallel use channel 106 of sheath 102, for example, by a threaded connector, a telescopic connector, or other interface designs. Multi-channel hub 114 is connected to the proximal end of parallel use channel 106 at a connection port 116, optionally a single connection port 116.

Multi-channel hub 114 including multiple working ports 118A-C, for example, 2, 3, 4, or larger number of ports. Multi-channel hub 114 provides access to parallel use channel 106 from each of working ports 118A-C. Each working port 118A-C may be selected for communication with parallel use channel 106 using connection port 116. As used herein, communication between a respective working port and parallel use channel 106 means established fluid and/or mechanical continuity from the respective working port to the distal end of parallel use channel 106, such that fluid may flow between the respective working port and the distal end of parallel use channel 106, and/or such that catheter-based tool 112 may be delivered to the distal end of parallel use channel 106 from the respective working port. Septum plugs, check valves and valves are optional for preventing back flow and cross contamination.

Optionally, working port 118A is implemented as a rinse port that couples to a fluid reservoir device that injects fluid, for example, a saline filled syringe or pump.

Optionally, working port 118B is implemented as a withdrawal port that couples to a vacuum forming device (or other low pressure sink) that removes fluid.

Optionally, working port 118C is implemented as a tool port for passing the catheter-based tool and/or a bendable wire.

Multi-channel hub 114 establishes a fluid channel for fluid communication between parallel use channel 106 and rinse port 118A or withdrawal port 118B, and a mechanical channel for passing therethrough the catheter-based tool between parallel use channel 106 and tool port 118C such that fluid from rinse port 118A or withdrawal port 118B and the catheter-based tool of tool port 118C are simultaneously passing all along parallel use channel 106.

An optional switch 120 toggles between working ports 118A-C for selection of an active working port in communication with parallel use channel 106.

Alternatively, each working port 118A-C is associated with an independent switch (e.g., valve) that controls whether the respective working port is in communication with parallel use channel 106. Alternatively, there is switch, and all working ports 118A-C are simultaneously in communication with parallel use channel 106.

Devices 108A-C may be coupled to respective working ports 118A-C. Each device 108A-C provides a respective function, which may be used to perform a respective procedural act when sheath 102 is inserted in the body of the patient. For example, a device may include a liquid (e.g., saline) reservoir, for injection of saline into the body of the patient using parallel use channel 106, for example, to rise off ablated tissue, or remove obstructions. In another example, a device may include a vacuum or suction, for extraction of liquid within the body of the patient through parallel use channel 106, for example, to suction blood out of a cavity of the patient. In another example, a device may include catheter-based tool 112, for performing manipulating tissue within the cavity of the patient, for example, ablation, cutting, injecting, and grabbing.

One or more working ports 118A-C may be designed as tool ports for insertion of catheter-based tool 112 into parallel use channel 106. Tool port(s) may include a septum designed to prevent leaks of fluid out of the tool port when the catheter-based tool is inserted into the parallel use channel.

One or more working ports 118A-C may be designed as liquid ports that are arranged for flow of liquid into and/or out of parallel use channel 106. The liquid ports are designed to prevent leaks of fluid when connecting to respective devices, for example, tubes, fluid suction, and a fluid reservoir. For example, liquid port may include a screw connection that provides a tight seal with the respective device.

Sheath 102 may include one or more illumination elements 122 located on the distal end portion thereof. Illumination elements 122 are designed to provide illumination (e.g., white light, selected spectral wavelengths) for endoscope 104 located within endoscope channel 110. Illumination elements 122 may be implemented, for example, as light emitting diodes (LED). Illumination elements 122 of sheath 102 may replace other illumination elements located on endoscope 104. Such endoscope without light source may be smaller and/or more compact than an endoscope that include light sources. The power supply (e.g., battery) and/or connection to a power supply (e.g., socket for connection to an external power source) 124 for powering illumination elements 122 may be implemented within multi-channel hub 114, and/or within another location on sheath 102.

Sheath 102 includes a transparent optical window 126 located at the distal end portion of endoscopic channel 126. Transparent optical window 126 is designed to prevent or reduce stray light from entering an imaging sensor of endoscopic device 104 located within endoscopic channel 110.

Figure 2:
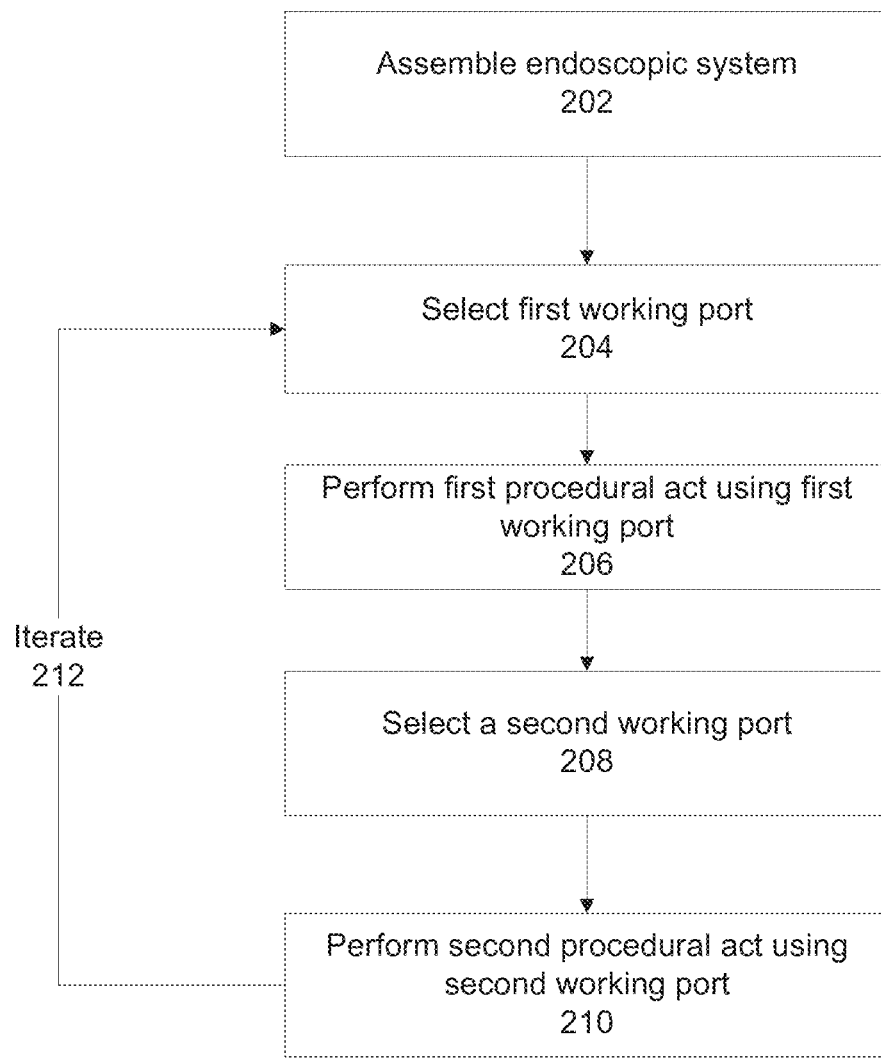
FIG. 2 is a flowchart of a method for operating the endoscopic system described with reference to FIG. 1, in accordance with some embodiments of the present invention.

Reference is now made to FIG. 2, which is a flowchart of a method for operating endoscopic system 100 (and/or sheath 102) described with reference to FIG. 1, in accordance with some embodiments of the present invention.

At 202, endoscopic system 100 is assembled.

Endoscope 104 is inserted into endoscopic channel 110 of sheath 102. For example, endoscope channel 110 (in folded or collapsed form) is retracted onto endoscope 104.

Multi-channel hub 114 is connected using connection port 116 to parallel use channel 106 of sheath 102 (when multi-channel hub 114 is provided as an independent component).

Devices 108A-C are attached to respective ports 118A-C of multi-channel hub 114.

At 204, a certain working port is selected. The selected port may include the rinse port or the withdrawal port. The certain working port may be activated (i.e., placed in fluid communication with parallel use channel 106) using switch 120 (which may be a central switch controlling all working ports, or the switch designed to operate only the certain working port). Alternatively, when there is no switch, the certain working port is implicitly selected by activating the respective device connection to the certain working port.

At 206, a certain procedural act is performed using parallel use channel 106 and fluid communication accessed from the certain working port. The certain procedural act is performed by activating the device associated with the certain working port. For example, derbies (and/to another fluid) are removed from the body of the patient by activation of a vacuum, and/or saline (and/to another fluid) is injected into the body of the patient by activation of a liquid reservoir.

At 208, another working port is selected. Optionally, the tool port is selected. The another working port is different than the certain working port selected in act 204. A mechanical channel is established for passing therethrough catheter-based tool 112 between parallel use channel 106 and the tool port.

At 210, another procedural act is performed using parallel use channel 106 accessed from the tool port. Catheter-based tool 112 is inserted and/or maneuvered within the body of the patient to tamper with tissue, for example, grab tissue, biopsy tissue, and ablate tissue.

At 212, blocks 204-210 are iterated when additional procedural acts are performed as part of the endoscopic procedure. For example, a cycle of saline injection, ablation, and removal of debris.

Blocks 206 and 210 (and additional iterations) may be performed sequentially. When the central switch is implemented, the central switch may be moved (at block 208) to cut-off the communication of the first device and first procedural port (selected in block 204) from parallel use channel 106 and provide communication for the second device and second procedural port. When individual switches are implemented, at 208 the switch for the first procedural port is moved to the closed position to cut-off communication of the first device and first procedural port from parallel use channel 106, and the switch from the second procedural port is moved to the open position to provide communication between the second device and second procedural port with parallel use channel 106.

Alternatively blocks 206 and 210 (and additional iterations) may be performed simultaneously. When the hub with no switches is implemented, devices may be simultaneously activated, for example, a vacuum is simultaneously operated with an ablation catheter to remove debris during an ablation procedure. When the hub with independent switches is implemented, the switches of the first and second operations ports may be opened sequentially or simultaneously, to allow simultaneous operation of the associated first and second devices.

Figure 3:
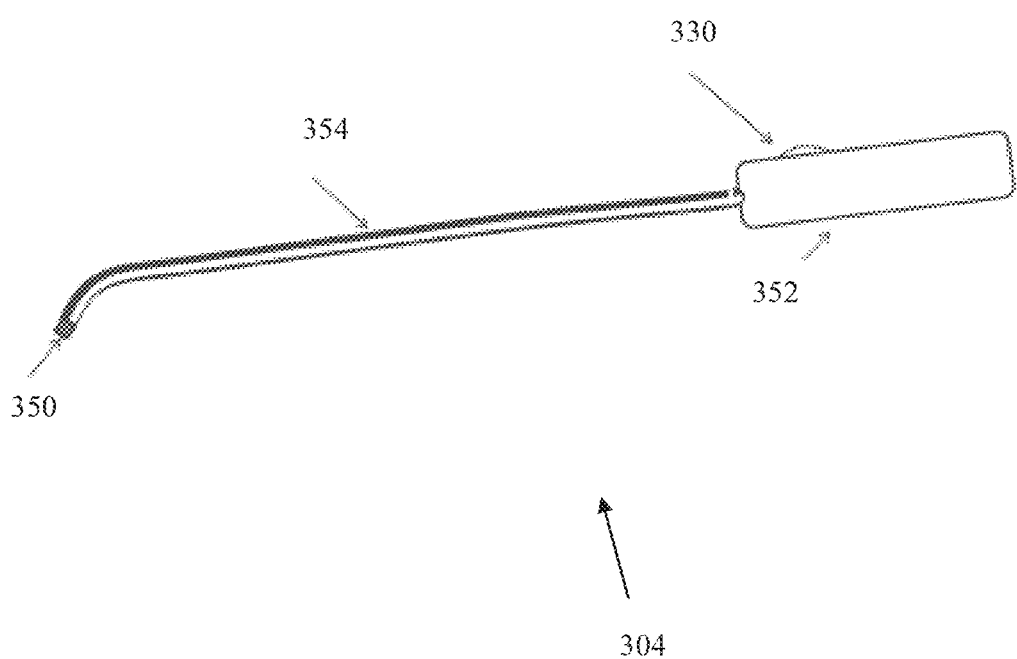
FIG. 3 is a schematic of an exemplary design of an endoscope used with the sheath as described with reference to FIG. 1 and/or FIG. 2, in accordance with some embodiments of the present invention.

Reference is now made to FIG. 3, which is a schematic of an exemplary design of an endoscope 304 used with the sheath as described with reference to FIG. 1 (corresponding to endoscope 104 and sheath 102) and/or FIG. 2, in accordance with some embodiments of the present invention. The endoscope 304 used with sheath 102 is designed to be low cost, have a small size, be mobile, and/or used with a short turnaround time, in comparison to traditional endoscopic towers that are more expensive, bulkier, are relatively fixed in position, and/or require cleaning and/or sterilization after each procedure.

Endoscope 304 does not include a work channel integrated within shaft 354. The parallel use channel is provided by the parallel use channel (e.g., parallel use channel 106) of the sheath (e.g., sheath 102), as described herein.

Endoscope 304 includes a thumb wheel 330 (corresponding to controller 130 of FIG. 1). Wheel 330 may adjust the direction of the distal end portion of endoscope 304, to control the viewing direction of an imaging sensor 350 located at the distal end portion.

A handle 352 of endoscope 304 is designed to be gripped and used for advancing endoscope 304. Handle 352 remains outside the body of the patient during the endoscopic procedure. Handle 352 may include an electrical interface for connecting with a display device (e.g., display device 132), for example, a USB port, an antenna, and/or a network interface.

Optionally, imaging sensor 350 is a high resolution imaging sensor, for example, having 4K resolution.

Endoscope 304 includes a flexible shaft 354 designed to navigate lumens of the body, to deliver imaging sensor 350 to a desired location within the body of the patient.

Figure 4:
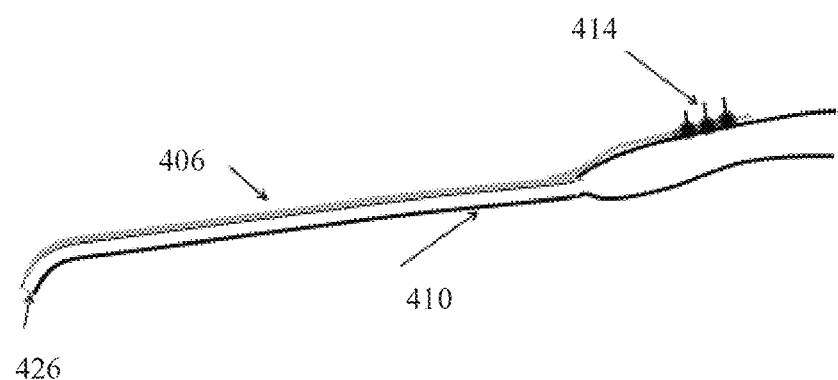
FIG. 4 is a schematic of an exemplary design of a sheath that incorporates a parallel use channel and a multi-channel hub, in accordance with some embodiments of the present invention.

Reference is now made to FIG. 4, which is a schematic of an exemplary design of a sheath 402 that incorporates a parallel use channel 406 and a multi-channel hub 414 (corresponding to sheath 102, parallel use channel 106, and multi-channel hub 114 described with reference to FIG. 1, and/or FIG. 2), in accordance with some embodiments of the present invention.

Sheath 402 includes an endoscopic channel 410 (corresponding to endoscopic channel 110 of FIG. 1) designed to house an endoscope during an endoscopic procedure.

A transparent optical window 426 (corresponding to window 126 of FIG. 1) is located on the distal end of endoscopic channel 410. Transparent optical window 426 is designed to prevent or reduce stray light from entering the imaging sensor located at the distal end portion of the endoscope housed within endoscopic channel 410.

Figure 5:
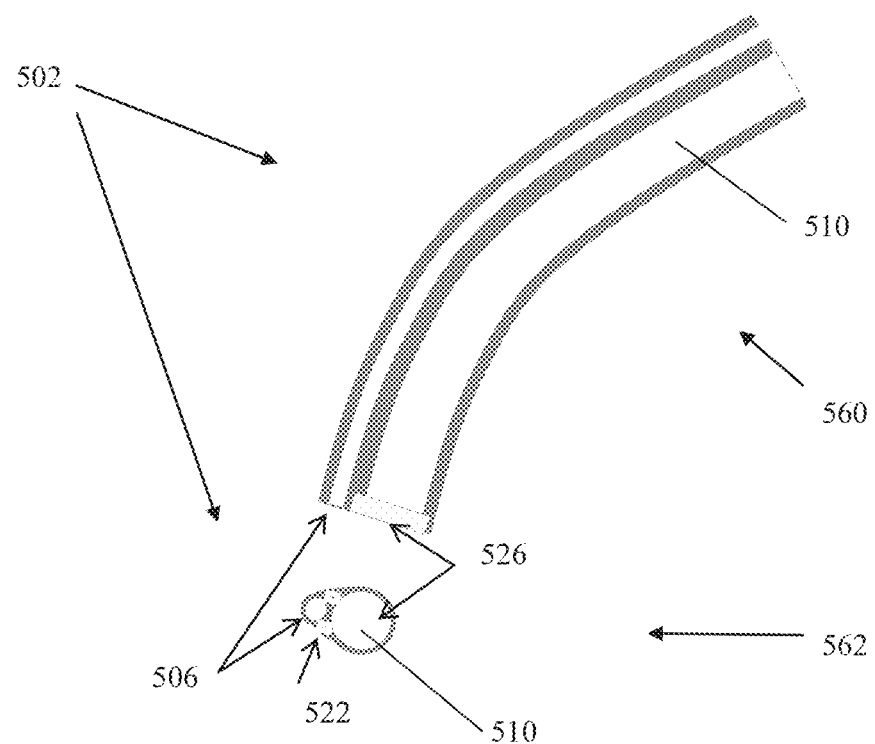
FIG. 5 is includes schematics depicting the distal end portion of a sheath, in accordance with some embodiments of the present invention.

Reference is now made to FIG. 5, which includes schematics depicting the distal end portion of a sheath 502 (corresponding to sheath 102 described with reference to FIG. 1 and/or sheath 402 described with reference to FIG. 4), in accordance with some embodiments of the present invention. Schematic 560 is a zoom-in side view of the sheath. Schematic 562 is a cross sectional and/or face-on view of the distal end of the sheath.

Sheath 502 includes a parallel use channel 506 (corresponding to parallel use channel 106 described with reference to FIG. 1 and/or parallel use channel 406 described with reference to FIG. 4), and an endoscopic channel 510 (corresponding to endoscopic channel 110 described with reference to FIG. 1 and/or endoscopic channel 410 described with reference to FIG. 4).

As shown, parallel use channel 506 is open at its distal end. The opening allows fluid (e.g., liquid) to flow in and/or out of parallel use channel 506 into and/or out from the body of the patient. The distal end (and the portion within the body) of endoscopic channel 526 is sealed to prevent contamination of the endoscope housed within the endoscopic channel of the sheath.

Sheath 502 includes a transparent optical window 526 located at the distal end of endoscopic channel 510 (corresponding to transparent optical window 126 described with reference to FIG. 1 and/or transparent optical window 426 described with reference to FIG. 4).

Sheath 502 includes one or more (two are depicted) illumination elements 522 (corresponding to illumination element 122 described with reference to FIG. 1), for example, LEDs.

Figure 6:
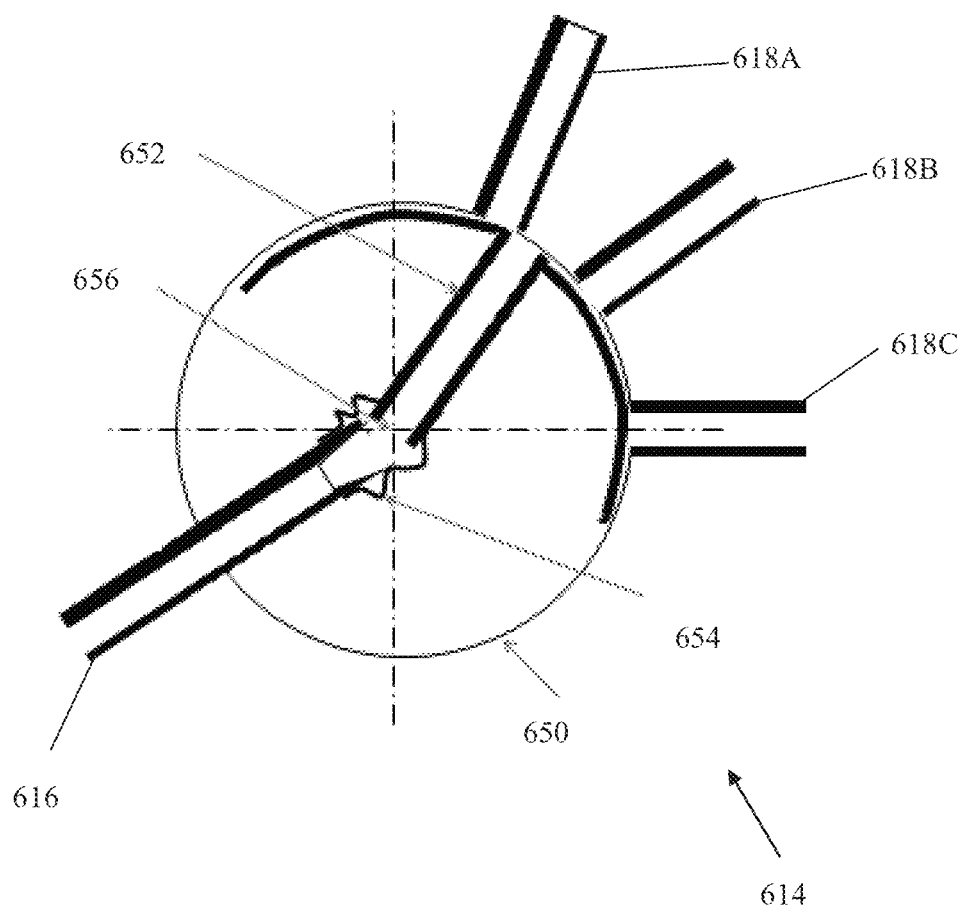
FIG. 6 is a schematic of an exemplary design of the multi-channel hub, in accordance with some embodiments of the present invention.

Reference is now made to FIG. 6, which is a schematic of an exemplary design 614 of the multi-channel hub (as described herein), in accordance with some embodiments of the present invention. Multi-channel hub 614 provides for selection of one of the working ports 618A-C by a housing of a rotation mechanism 650 that adjusts the position of a linking channel 652. Rotation mechanism 650 may be implemented as a distributor type selector switch that is manually and/or automatically adjusted to select one of the working ports 618A-C. A flexible element 654 (e.g., a bellows, a rubber tube, a spring) provides rotational movement of linking channel 652 at a rotating axis center 656. Linking channel 652 provides fluid and/or mechanical communication between the selected working port and a connection port 616 which is in fluid and/or mechanical communication with the parallel use channel of the sheath. The other (i.e., non-selected) working ports are blocked by the housing of rotation mechanism.

Figure 7A:
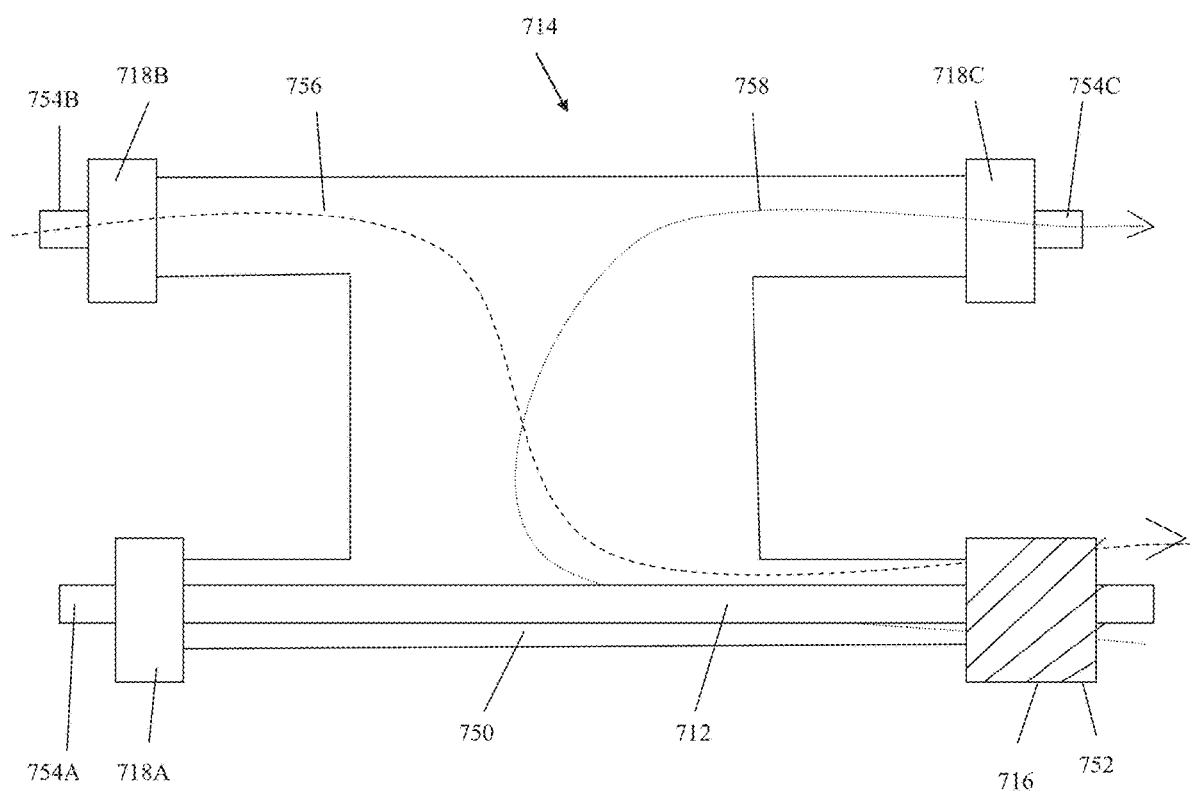
FIG. 7A is a schematic of another exemplary design of the multi-channel hub, in accordance with some embodiments of the present invention.

Reference is now made to FIG. 7A, which is a schematic of another exemplary design 714 of the multi-channel hub (as described herein), in accordance with some embodiments of the present invention. Multi-channel hub 714 is designed for simultaneous access of the parallel use channel of the sheath by working ports 718A-C simultaneously accessing connection port 716. The fluid and/or mechanical communication between working ports 718A-C and connection port 716 is provided by a common cavity 750 within multi-channel hub 714, for example, multi-channel hub 714 includes a hollow interior.

Connection port 716 is designed to connect to the parallel use channel of the sheath. Optionally, connection port 716 includes an interface designed to attach to the proximal end of the parallel use channel of the sheath, for example, a threaded connector 752.

Multi-channel hub 714 may be arranged in the shape of the letter H. Three arms of the H include working ports 718A-C, and the fourth arm includes connection port 716. Optionally, working port 718A is designed as a tool port, for example, including an interface 754A designed for introduction of catheter-based tools.

Optionally, tool port 718A and connection port 716 are located on opposite arms of the H multi-channel hub 714 along the straight longitudinal axis between the opposite arms. Catheter-based tool 712 may be inserted into the parallel use channel of the sheath by being advanced in a relatively straight line, through tool port 718A, cavity 750 of multi-channel hub 714, and connection port 716.

The other arms of the H may including working ports 718B-C designed for injection (represented by arrow 756) and/or suction of fluid (represented by arrow 758) into the parallel use channel of the sheath. Fluid ports 718B-C may include respective interfaces 754B-C for connection to fluid devices, for example, a tubes connecting to a vacuum source and/or a tube connection to a liquid reservoir.

Optionally, septum plugs, check valves and/or valves are included (optionally within ports 718A-C, or other locations within multi-channel hub 714), designed for the prevention of mixing and back flow of fluid flowing through multi-channel hub 714.

Figure 7B:
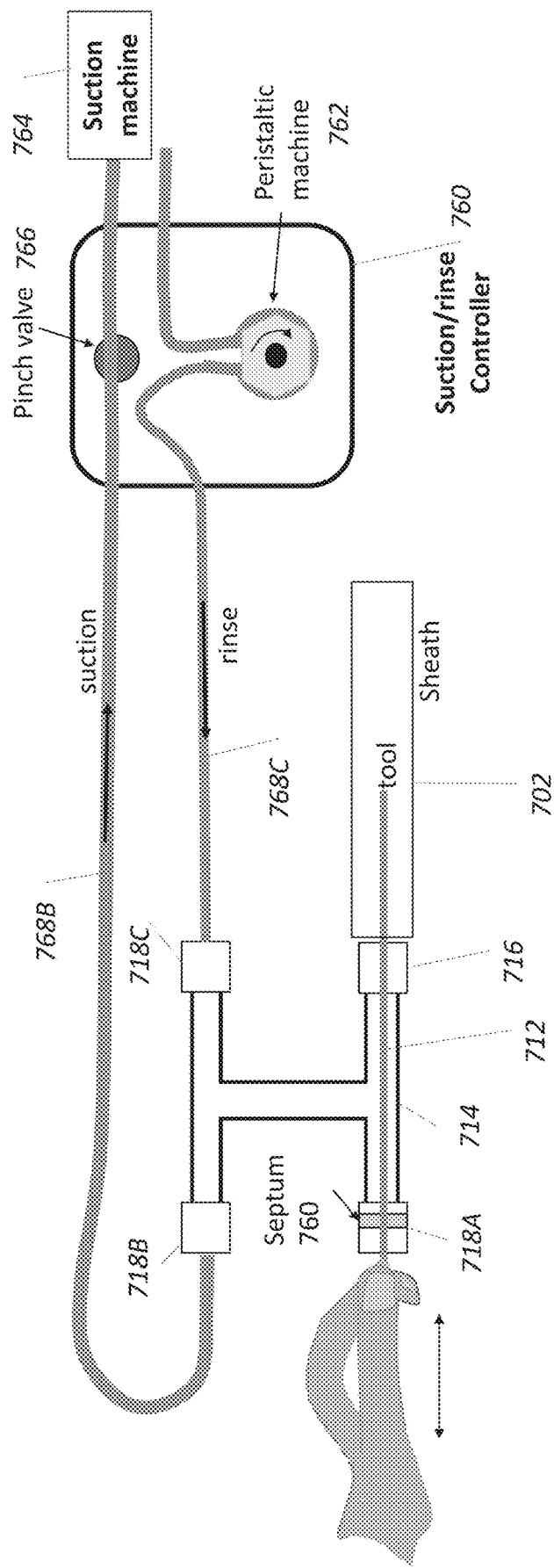
FIG. 7B is a schematic of the H shaped multi-channel hub described with reference to FIG. 7A connected to external devices, in accordance with some embodiments of the present invention.

Reference is now made to FIG. 7B, which is a schematic of the H shaped multi-channel hub 714 described with reference to FIG. 7A connected to external devices, in accordance with some embodiments of the present invention. FIG. 7B depicts an exemplary set-up for connecting external devices to a sheath 702 (as described herein, for example, with reference to sheath 102 of FIG. 1) using the H shaped multi-channel hub 714. Multi-channel hub 714 is connected to the parallel use channel of sheath 702 using connection port 716, as described herein.

A device 760 includes a peristaltic machine 762 designed to pump liquid (e.g., water, saline, other liquids) into sheath 702, and a suction machine 764 (e.g., vacuum source) designed to remove liquid and/or other fluid from sheath 702. A pinch valve 766 controls the activation of the suction. Device 760 is connected to working ports 718B-C using respective tubes 768B-C.

Tool 712 is inserted into sheath 702 through tool port 718A that includes a septum 770 designed to prevent leaks of the liquid being inserted or removed by device 760.

Figure 7C:
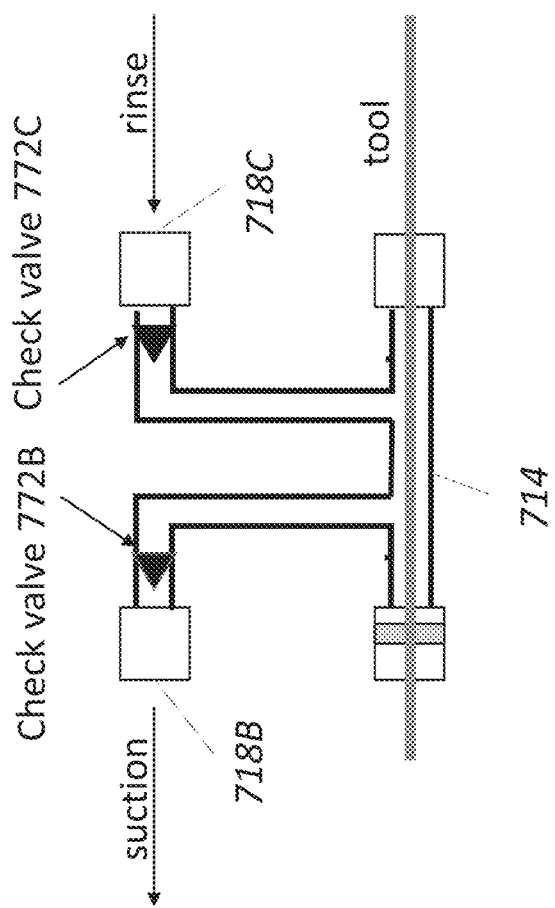
FIG. 7C is a schematic of the H shaped multi-channel hub described with reference to FIGS. 7A-7B, including check valves installed in association with working ports, in accordance with some embodiments of the present invention.

Reference is now made to FIG. 7C, which is a schematic of the H shaped multi-channel hub 714 described with reference to FIGS. 7A-7B, including check valves 772B-C installed in association with working ports 718B-C (which are used to insert and/or remove liquid), in accordance with some embodiments of the present invention. Check valves 772B-C are positioned for one way flow of fluid. Check valves 772B-C are designed to prevent mixing of injected and removed liquid, and to prevent back-flow of the liquid. Check valve 772B is designed to allow liquid to flow out of multi-channel hub 714 (e.g., into device 760) when working port 718B is used for suction. Check valve 772C is designed to allow liquid to flow into multi-channel hub 714 (e.g., from device 760) when working port 718C is used for rinsing.

Figure 8:
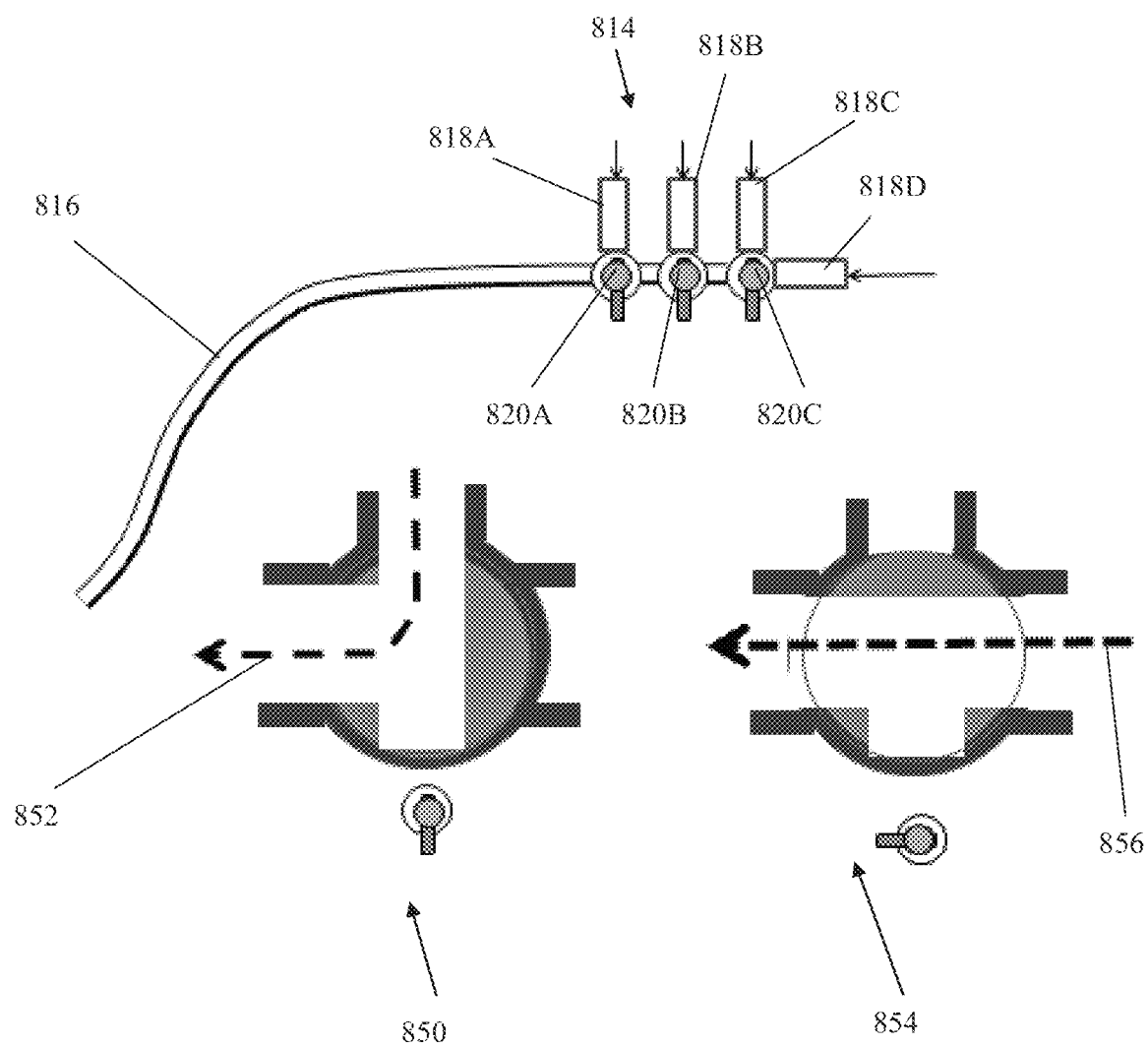
FIG. 8 is a schematic of another exemplary design of the multi-channel hub, in accordance with some embodiments of the present invention.

Reference is now made to FIG. 8, which is a schematic of another exemplary design 814 of the multi-channel hub (as described herein), in accordance with some embodiments of the present invention. Multi-channel hub 814 includes working ports 818A-C each with a respective switch 820A-C that provide fluid and/or mechanical communication between the respective working port and communication port 816 that connects to the parallel use channel of the sheath. Each switch 820A-C is independently controlled and activated.

Optionally, switch 820C connects to two working ports 818C and 818D, for selecting one of working ports 818C-D for communication with communication port 816 and the parallel use channel.

Working port 818D may be designated as a tool port for insertion of catheter-based tools. The longitudinal axis of working port 818D is aligned with the longitudinal axis of communication port 816, providing for easy advancement of a catheter-based tool when working port 818D is placed in fluid and/or mechanical communication with communication port 816 by switch 820C.

Working ports 818A-C may be designated as fluid ports for injection and/or removal of fluid and/or liquid from communication port 816 (and from the parallel use channel of the sheath).

Schematic 850 depicts the switch (i.e., one or more of switches 820A-C) in an active position that places the respective fluid port (i.e., one or more of 818A-C) in fluid and/or mechanical communication with communication port 816 (and the parallel use channel of the sheath). Fluid is able to flow in the direction of arrow 852 or in the reverse direction of arrow 852.

Schematic 854 depicts the switch (i.e., one or more of switches 820A-C) in closed position that disconnects the respective fluid port (i.e., one or more of 818A-C) from fluid and/or mechanical communication with communication port 816 (and the parallel use channel of the sheath). The closed position of the switch establishes fluid and/or mechanical communication with other working ports located proximally to the switch and communication port 816. As shown by arrow 856, fluid is able to flow across the switch without entering the working port of the switch. Alternatively, in the setup of tool port 818D and switch 820C, schematic 854 depicts switch 820C activating tool port 818D such that the catheter-based tool is advanced in the direction of arrow 856 into communication port 816 and the parallel use channel of the sheath, or in the reverse direction of arrow 856.

Figure 9:
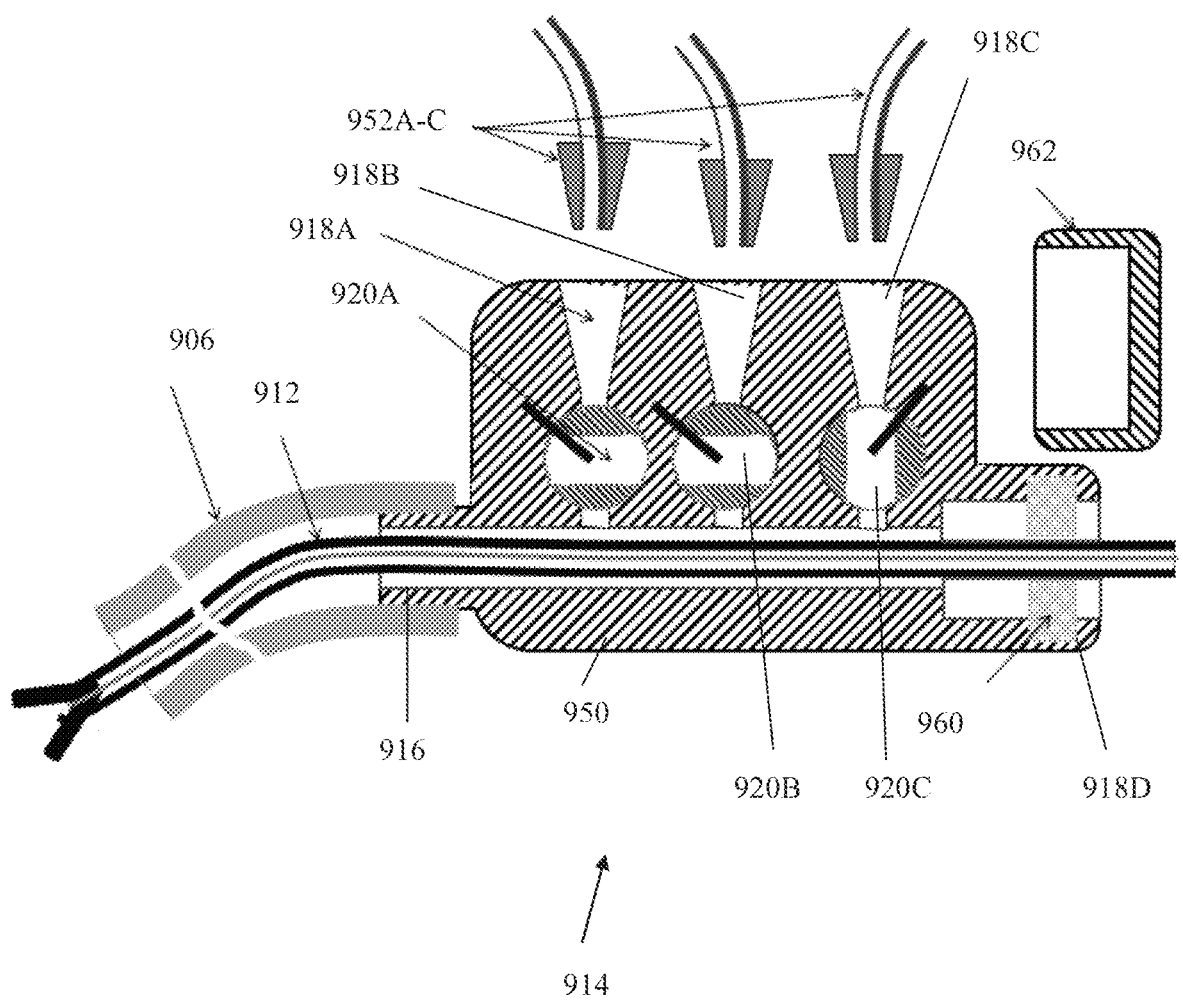
FIG. 9 is a schematic of another exemplary design of the multi-channel hub, in accordance with some embodiments of the present invention.

Reference is now made to FIG. 9, which is a schematic of another exemplary design 914 of the multi-channel hub (as described herein), in accordance with some embodiments of the present invention. Multi-channel hub 914 includes a hub body 950 designed for simultaneous use for fluid (e.g., liquid) insertion and/or removal, and for insertion of a catheter-based tool 912 into a parallel use channel 906 of the sheath using a connection port 916.

Working ports 918A-C are designated as fluid ports, designed to connect with tubes 952A-C that deliver fluid or remove fluid. Switches 920A-C, designed as valves, independently open or close fluid communication with parallel use channel 906 and the respective tube 952A-C. Simultaneous fluid communication with parallel use channel 906 and one, two, or all three tubes 952A-C is controlled by respective valves 920A-C.

A working port 918D is designated as a tool port for introduction of catheter-based tool 912 into parallel use channel 906. A septum 960 is designed to prevent leaks of fluid out of tool port 918D when catheter-based tool 916 is inserted into parallel use channel 906. Septum 960 may be implemented, for example, as a rubber stopper with a hole that forms a seal around catheter-based tool 912. An optional cover 962 is designed to fit on tool port 918D when no catheter-based tool 912 is being used.

Figure 10:
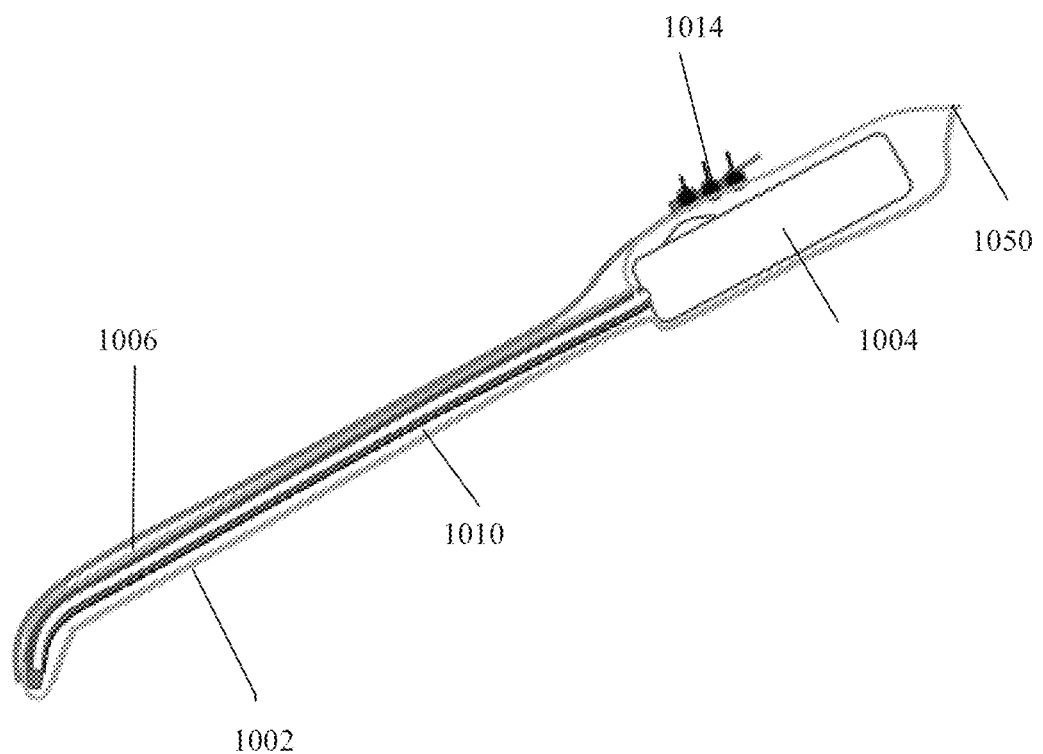
FIG. 10 is a schematic of an endoscope inserted into an endoscopic channel of a sheath that includes a parallel use channel and multi-channel hub, in accordance with some embodiments of the present invention.

Reference is now made to FIG. 10, which is a schematic of an endoscope 1004 inserted into an endoscopic channel 1010 of a sheath 1002 that includes a parallel use channel 1006 and multi-channel hub 1014, in accordance with some embodiments of the present invention. Sheath 1002 may be secured at its proximal end portion 1050, or left open, since end portion 1050 remains outside the body of the patient.

Figure 11:
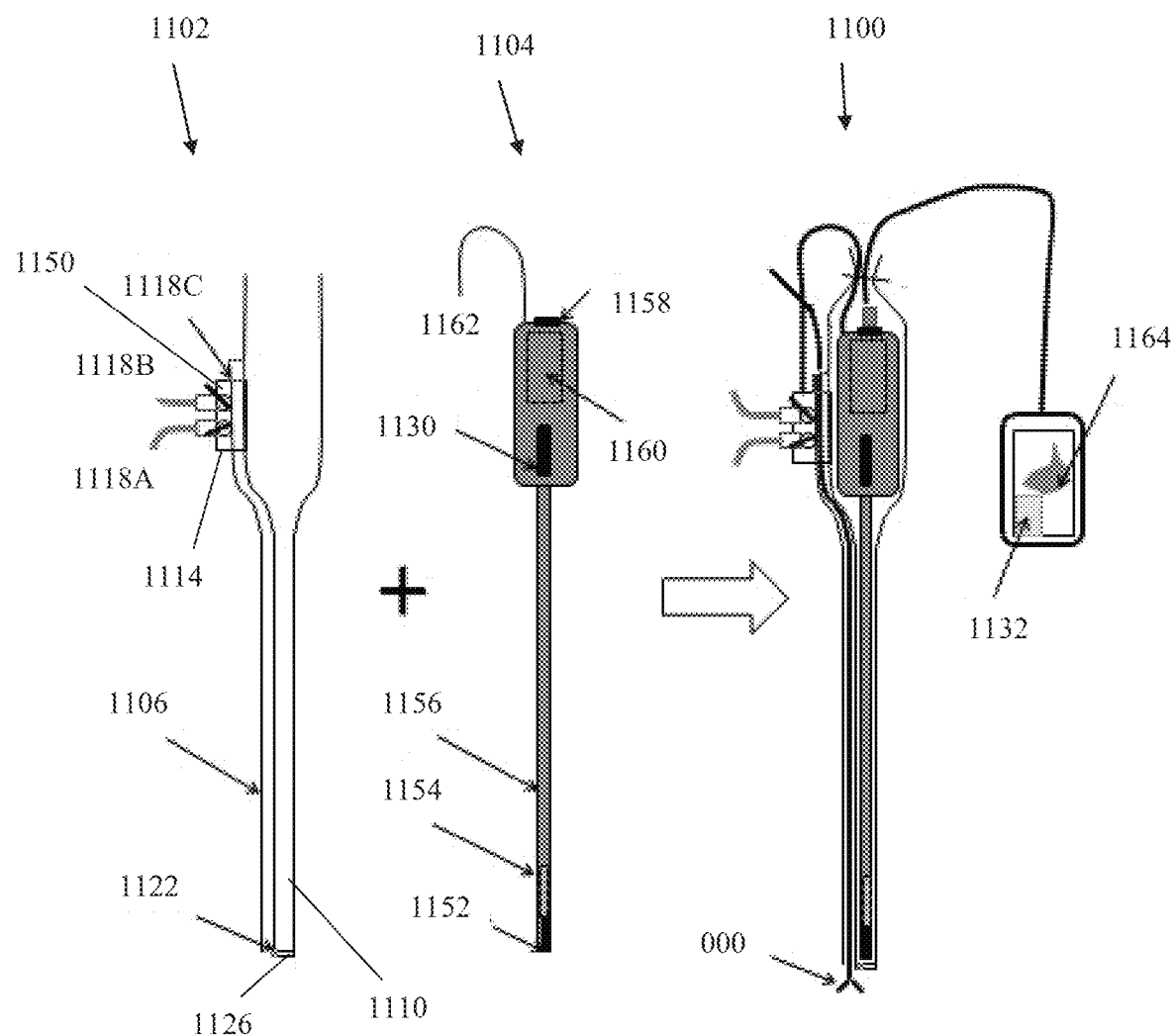
FIG. 11 is a schematic depicting assembly of an endoscopic system by insertion of an endoscope into a sheath, in accordance with some embodiments of the present invention.

Reference is now made to FIG. 11, which is a schematic depicting assembly of an endoscopic system 1100 by insertion of an endoscope 1104 into a sheath 1102, in accordance with some embodiments of the present invention. Details of components of endoscopic system 1100 are described herein.

Sheath 1102 includes a parallel use channel 1106 that is accessible individually or simultaneously by one or more working ports 1118A-C under control a multi-channel hub 1114, as described herein. Optionally, working ports 1118A-B are designed for fluid delivery and/or application of vacuum. Optionally, working port 1118C is designed as a tool port for insertion of a catheter-based tool into parallel use channel 1106. Multi-channel hub 1114 may include a power source (e.g., plug, battery) 1150 that powers illumination element(s) 1122 (e.g., LEDs) located at the distal end portion of sheath 1102. Sheath 1102 includes a transparent optical window at the distal end portion of an endoscopic channel 1110.

Endoscope 1104 includes an imaging sensor (e.g., high resolution camera) 1152 at the distal end portion. Endoscope 1104 includes a flexible segment 1154 and a flexible shaft 1156 designed for navigating around tortuous anatomical channels of the body of the patient. The proximal end portion of endoscope 1104 includes a controller 1130 (e.g., thumb wheel), an electrical interface 1158 and electrical components 1160, for example, USB port, an antenna, and a network interface.

Endoscope 1104 may include a power cable 1162, which may connect to power source 1150 of sheath 1102 when endoscope 1104 is inserted within endoscopic channel 1110 of sheath 1102.

System 1100 is assembled by placing endoscope 1104 within endoscopic channel 1110 of sheath 1102. A display device 1132 (e.g., smartphone, tablet computer), is electrically connected to endoscope 1104 using interface 1158. Image(s) 1164 captured by imaging sensor 1152 are presented on display device 1132.

It is expected that during the life of a patent maturing from this application many relevant endoscopes and catheter-based tools will be developed and the scope of the terms endoscope and catheter-based tool are intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this present invention may be presented in a range format. It should be understood that the description in range format is merely for convenience and brevity and should not be construed as an inflexible limitation on the scope of the present invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the present invention, which are, for clarity, described in the context of separate embodiments, may also be provided in combination in a single embodiment. Conversely, various features of the present invention, which are, for brevity, described in the context of a single embodiment, may also be provided separately or in any suitable subcombination or as suitable in any other described embodiment of the present invention. Certain features described in the context of various embodiments are not to be considered essential features of those embodiments, unless the embodiment is inoperative without those elements.

Although the present invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A multi-channel hub of a compound sheath for encasing an endoscope during an endoscopic procedure, comprising:
    a connection port that is configured to couple to a proximal end of a parallel use channel of a compound sheath;
    a rinse port that couples to a fluid reservoir device that injects fluid;
    a withdrawal port that couples to a vacuum forming device that removes fluid;
    a tool port for receiving a catheter-based tool;
    a fluid channel sized and shaped to establish a fluid communication between the parallel use channel, the connection port, the rinse port and the withdrawal port, wherein fluid injected through the rinse port passes along the fluid channel through the connection port and into the parallel use channel, and fluid withdrawn through the withdrawal port passes from the parallel use channel through the connection port;

a mechanical channel sized and shaped to pass therethrough a catheter-based tool, between the tool port and the connection port; and at least one switch for selecting which of the rinse port, withdrawal port, and tool port is in communication with the parallel use channel using the connection port;

wherein the fluid channel and the mechanical channel both include the connection port;

wherein the at least one switch is operated by rotation of a linking channel between the rinse port, withdrawal port, and tool port and the connection port.

2. The multi-channel hub of claim 1, further comprising a septum disposed at the tool port to prevent leaks of fluid out of the tool port when the catheter-based tool is inserted into the parallel use channel and fluid is flowing in the parallel use channel from the rinse port or to the withdrawal port.

3. The multi-channel hub of claim 1, wherein each of the rinse port, the withdrawal port, the connection port and the tool port is formed in one of a set comprising four separated arms formed in a common hub housing.

4. The multi-channel hub of claim 3, wherein the tool port and the connection port are on a common longitudinal axis.

5. The multi-channel hub of claim 1, wherein the rinse port includes a first check valve designed to allow flow of liquid into the multi-channel hub and prevent backflow of liquid out of the multi-channel hub and the withdrawal port includes a second check valve designed to allow flow out of liquid out of the multi-channel hub and prevent backflow of liquid into the multi-channel hub.

6. The multi-channel hub of claim 1, further comprising at least one illumination element located on a distal end portion of the compound sheath; so as to illuminate the endoscope, and a transparent optical window at the distal end portion of an endoscopic channel formed within the compound sheath, so as to prevent or reduce stray light from entering an image sensor of the endoscope.

7. The multi-channel hub of claim 6, further comprising a power supply socket that supplies electrical power to the at least one illumination element.

8. The multi-channel hub of claim 6, wherein the compound sheath further comprises an endoscopic channel arranged as a first elongated lumen sized for accepting an elongated endoscopic imaging device;

wherein the parallel use channel is arranged as a second elongated lumen sized for accepting the catheter-based tool, the walls of the parallel use channel arranged for flow of fluid through the parallel use channel;

wherein the endoscopic channel and the parallel use channel are arranged parallel to each other along a longitudinal axis of the compound sheath;

wherein the parallel use channel is open at the distal end thereof to provide fluid and mechanical communication between the parallel use channel and the body of the patient external to the multi-channel hub, and the endoscopic channel is closed to prevent fluid communication between the endoscopic channel and the body of the patient external to the multi-channel hub.

9. The multi-channel hub of claim 1, wherein at least one of the rinse port and the withdrawal port includes a valve that controls the fluid communication between the respective rinse port or withdrawal port and the connection port.

10. The multi-channel hub of claim 1, wherein the fluid channel and mechanical channel are operable simultaneously, such that the catheter-based tool and at least one of:

1) fluid entering the parallel use channel from the rinse port through the connection port, and 2) fluid drawn from the parallel use channel and through the connection port to the withdrawal port, are simultaneously passing along the parallel use channel.

* * * * *